United States Patent
Cramail et al.

(10) Patent No.: US 9,029,494 B2
(45) Date of Patent: May 12, 2015

(54) CASTOR OIL DERIVATIVES AND METHOD FOR THE PRODUCTION THEREOF

(75) Inventors: Henri Cramail, Pessac (FR); Aurélie Boyer, Bordeaux (FR); Eric Cloutet, Saint Caprais de Bordeaux (FR); Carine Alfos, Pessac (FR)

(73) Assignee: Centre National de la Recherche Scientifique (C.N.R.S), Paris (FR)

( * ) Notice: Subject to any disclaimer, the term of this patent is extended or adjusted under 35 U.S.C. 154(b) by 492 days.

(21) Appl. No.: 13/395,279

(22) PCT Filed: Sep. 10, 2010

(86) PCT No.: PCT/FR2010/051893
§ 371 (c)(1),
(2), (4) Date: Sep. 12, 2012

(87) PCT Pub. No.: WO2011/030075
PCT Pub. Date: Mar. 17, 2011

(65) Prior Publication Data
US 2013/0005936 A1    Jan. 3, 2013

(30) Foreign Application Priority Data
Sep. 11, 2009 (FR) ................................... 09 56258

(51) Int. Cl.
C08G 18/10 (2006.01)
C08G 18/67 (2006.01)
C07C 51/00 (2006.01)
C11C 3/04 (2006.01)
C07C 67/03 (2006.01)
C07C 69/732 (2006.01)
C08G 18/36 (2006.01)
C11C 3/00 (2006.01)

(52) U.S. Cl.
CPC . *C11C 3/04* (2013.01); *C07C 67/03* (2013.01); *C07C 69/732* (2013.01); *C08G 18/36* (2013.01); *C11C 3/003* (2013.01)

(58) Field of Classification Search
USPC ..................................... 528/75; 554/168, 219
See application file for complete search history.

(56) References Cited

U.S. PATENT DOCUMENTS 2,902,500 A * 9/1959 Smith ........................... 554/168
4,125,545 A * 11/1978 Kroplinski et al. ........... 554/106
5,306,788 A * 4/1994 Uchida et al. ............ 525/440.06

OTHER PUBLICATIONS

Pena, R. et al.: Transesterification of Castor Oil: Effect of Catalyst and Co-Solvent, Industrial & Engineering Chemistry Research, vol. 48, No. 3, Sep. 30, 2008, pp. 1186-1189.*
Lyon, Cameron K. et al: Diol diricinoleates from dihaloalkanes, Journal of the American Oil Chemists' Society, vol. 47, No. 4, 1970, pp. 145-146.*
Lyon et al., "Diol Dirichinoleates from Dihaloalkanes" Journal of American Oil Chemists' Society, 1970, pp. 145-146, vol. 47, No. 4, XP002565322.
Pena et al., "Transesterification of Castor Oil: Effect of Catalyst and Co-Solvent", Industrial & Engineering Chemistry Research, Sep. 2008, pp. 1186-1189, vol. 48, No. 3, XP002616422.

* cited by examiner

Primary Examiner — Deborah D Carr
(74) Attorney, Agent, or Firm — Young & Thompson

(57) ABSTRACT

Novel compounds of formula (1) wherein: A is especially a linear or branched divalent alkylene radical having between 1 and 10 carbon atoms, and Y is especially a hydrogen atom.

6 Claims, No Drawings

CASTOR OIL DERIVATIVES AND METHOD FOR THE PRODUCTION THEREOF

The object of the present invention is novel castor oil derivatives as well as their preparation method.

There exist different approaches for synthesizing polymers based on vegetable oils. The first most widespread one consists of considering triglycerides as base materials, the latter may be epoxidized and for example alcoholized or hydroformylated in order to make them functional and polymerizable.

An oil is a mixture of triglycerides (triesters) formed by condensation of fatty acids and of glycerol. The high number of fatty acid types (up to 24) present in each fat and the multiple possibilities of their combinations with glycerol molecules have the result that the fats are highly complex mixtures of compounds, the properties of which vary from one oil to another. The nature of the triglycerides may therefore vary within a same oil.

The reactive sites present in a triglyceride are mainly double bonds and ester functions. The reactivity of double bonds allows introduction of hydroxyl functions, thereby allowing access to polyhydroxylated monomers. Nevertheless, it is impossible to obtain triglycerides having perfectly defined structures and functionalities.

The object of the present invention is to provide a method for preparing compounds from vegetable oil, with which the aforementioned drawbacks may be overcome.

The object of the present invention is also to provide a method for preparing compounds derived from vegetable oil, comprising the use of catalysts better fitting environmental expectations than most of the homogeneous catalysts used and which limit the secondary reactions.

The object of the present invention is also to provide a method which, unlike the methods of the prior art which relate to chemical transformation from triglycerides having poorly defined structures, consist in a simple and efficient way of chemically modifying monoesters or triglycerides in order to obtain functional precursors with controlled functionality.

The object of the present invention is to provide a simple method allowing access to novel synthons, mono-esters or di-esters, having well defined structures and resorting to clean catalysis.

The present invention relates to compounds of the following formula (I):

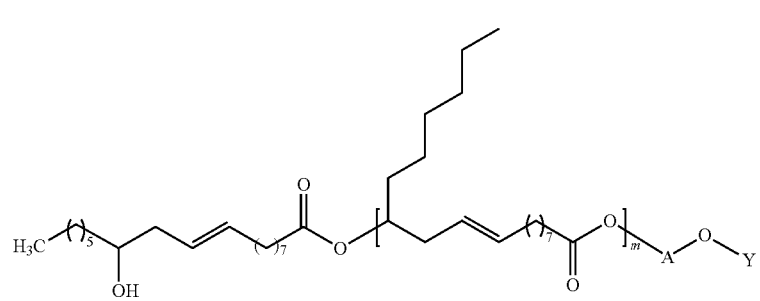

wherein:
m is equal to 0 or is an integer n comprised between 1 and 20:
A represents a linear or branched divalent alkylene radical, comprising from 1 to 10 carbon atoms, and optionally interrupted by one or more heteroatoms, and more particularly by one or more oxygen atoms, and
Y represents a hydrogen atom or a group of formula (II)

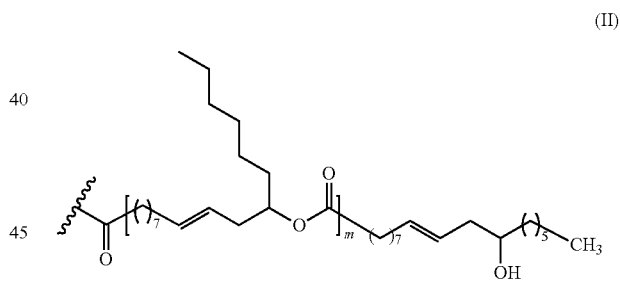

m being as defined above in formula (I).

Thus, in the formula (I), when m is equal to 0, the present invention relates to compounds of the following formula (Ib is):

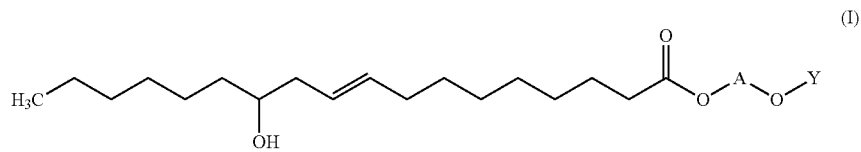

A and Y being as defined above in formula (I).

Among the compounds of the invention, mention may notably be made of monoester compounds of the following formula (I-1):

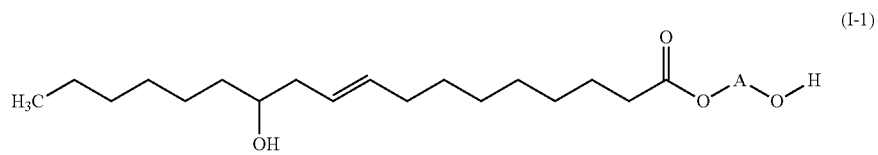
(I-1)

A being as defined above in formula (I).

Preferably, in formula (I-1), A represents a linear or branched divalent alkylene radical, comprising from 1 to 10 carbon atoms, interrupted by at least one oxygen atom.

Among the compounds of the invention, mention may also notably be made of diester compounds of the following formula (I-2):

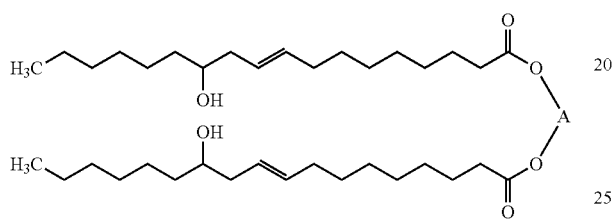
(I-2)

A being as defined above in formula (I).

Preferably, in formula (I-2), A represents a linear or branched divalent alkylene radical, comprising from 1 to 10 carbon atoms, interrupted by at least one oxygen atom.

The present invention also relates to the compounds of the following formula (I-3):

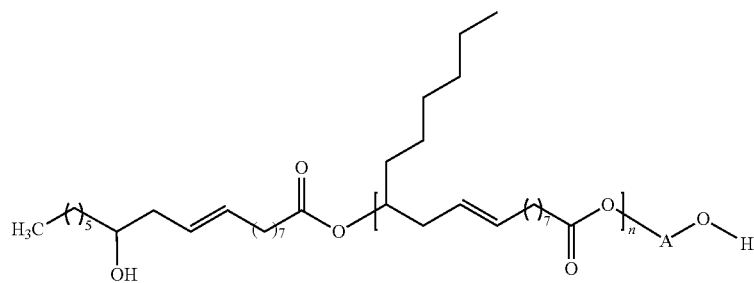
(I-3)

n and A being as defined above in formula (I).

The present invention also relates to the compounds of the following formula (I-4):

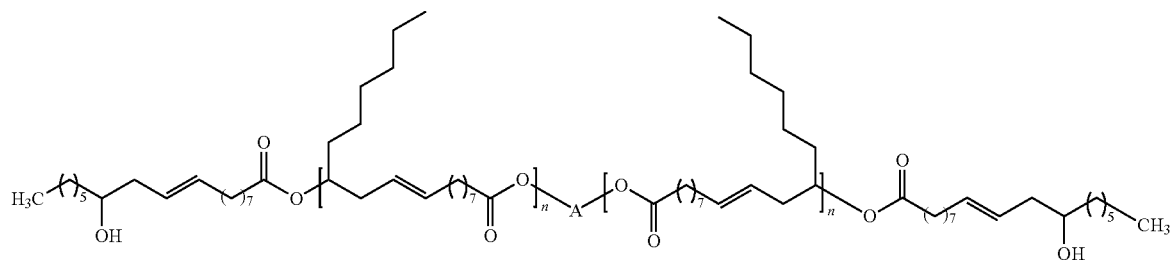
(I-4)

n and A being as defined above in formula (I).

According to a preferred embodiment, the present invention also relates to compounds fitting one of the formulae (I), (I-1), (I-2), (I-3) or (I-4) wherein A represents an alkylene radical comprising 3 or 4 carbon atoms.

According to a preferred embodiment, the present invention also relates to compounds fitting one of the formulae (I), (I-1), (I-2), (I-3) or (I-4) wherein A represents a (poly)propyleneglycol.

The present invention relates to a method for preparing a compound of formula (I-1) as defined above, comprising a step for transesterification of castor oil with a diol of the following formula (III) HO-A-OH, A being as defined above in formula (I-1).

The present invention also relates to a method for preparing a compound of formula (I-1) as defined above, comprising a step for transesterification of castor oil with a diol of the following formula (III) HO-A-OH, A represents a linear or branched divalent alkylene radical, comprising from 1 to 10 carbon atoms, interrupted by at least one oxygen atom.

According to an advantageous embodiment, the transesterification step of the method of the invention is carried out in the presence of a transesterification catalyst.

According to a particularly advantageous embodiment, the transesterification catalyst applied within the scope of the method of the invention is selected from the group consisting of magnesium oxide, zinc acetate, titanium tetraalkoxide, notably titanium tetrabutoxide, and sodium methanolate.

Preferably, in order to prepare the compounds of the aforementioned formula (I-1), the diol of formula (III) is used in excess. Thus, more particularly, the ratio between the number of moles of the diol and the number of moles of castor oil is comprised from 10 to 100.

The present invention also relates to a method for preparing a compound of formula (I-2) as defined above, comprising the following steps:
a step a) for transesterification of castor oil with an alcohol ROH, R representing a linear or branched alkyl group, comprising from 1 to 10, preferably from 1 to 6 carbon atoms in order to obtain a compound of the following formula (IV):

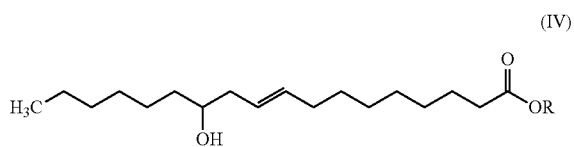

and a step b) for transesterification of the compound of formula (IV) with a diol of the following formula (III) HO-A-OH, A representing a linear or branched divalent alkylene radical, comprising from 1 to 10 carbon atoms and optionally interrupted by one or more heteroatoms, and more particularly by one or more oxygen atoms.

According to a preferred embodiment, step b) of the method of the present invention is carried out in the presence of a transesterification catalyst.

In a particularly advantageous way, said transesterification catalyst is selected from the group consisting of magnesium oxide, zinc acetate, titanium tetraalkoxide, preferably titanium tetrabutoxide, and sodium methanolate.

Preferably, in order to prepare the compounds of the aforementioned formula (I-2), the diol of formula (III) is used by default. Thus, more particularly, the ratio between the number of moles of the diol and the number of moles of castor oil is comprised from 0.2 to 3.

The present invention also relates to a method for preparing a compound of formula (I-2)

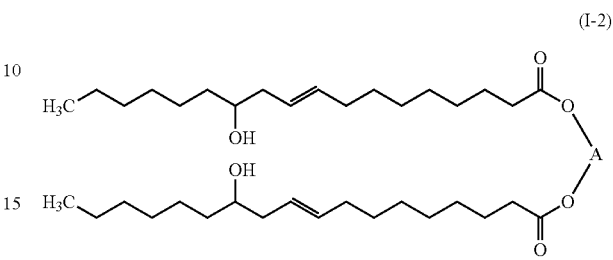

A being as defined above in formula (I),
said method comprising the following steps:
a step a) for transesterification of castor oil with an alcohol ROH, R representing a linear or branched alkyl group, comprising from 1 to 10, preferably from 1 to 6 carbon atoms in order to obtain a compound of the following formula (IV):

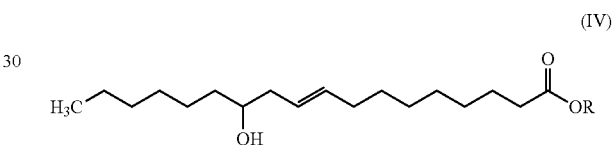

a step a1) for reacting the compound (IV) with sodium methanolate in order to obtain a compound of the following formula (V):

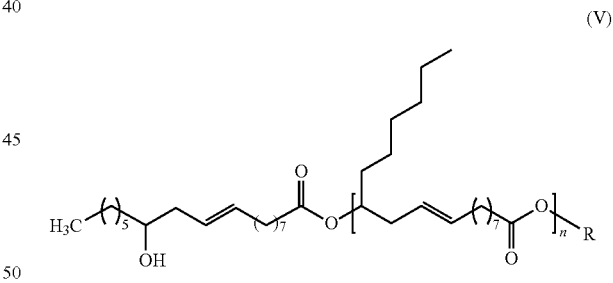

n being as defined in formula (I),
and a step b) for transesterification of the compound of formula (V) with a diol of the following formula (III) HO-A-OH, A representing a linear or branched divalent alkylene radical, comprising from 1 to 10 carbon atoms, and optionally interrupted by one or more heteroatoms, and more particularly by one or more oxygen atoms.

Preferably, according to the preparation method of the present invention, step a1) is carried out at a temperature comprised between 100° C. to 220° C.

Within the scope of the method according to the present invention, it is particularly advantageous to carry out the reactions with heterogeneous catalysis, for example with magnesium oxide, which allows the catalyst to be filtered after the reaction and therefore to be removed from the reaction medium.

According to another advantageous embodiment, the compounds of the invention are prepared according to a method applying a titanium-based catalyst, and more particularly Ti(OBu)$_4$ which has interesting properties in terms of viscosity.

The aforementioned compounds of the invention are polyols containing at least two OH functions which may be used inter alia as monomers. With their purity it is possible to optimize the properties of the obtained polymers.

Thus, polyurethanes were then synthesized by bulk polymerization of these polyols with IPDI (or for example also with MDI or HDI), at 60° C. in the presence of tin dibutyl dilaurate. The formation of the polyurethanes is confirmed by FTIR with disappearance of the vibration band of the isocyanate. Steric exclusion chromatography confirms molar masses comprised between 14,000 and 50,000 g/mol. These di-OH monomers may also be used for synthesizing other polymers such as polyesters, polyethers, polycarbonates, etc.

The compounds according to the present invention of formula (I), (I-1) or (I-2) are notably used for reacting with polyisocyanates for preparing polymers notably polyurethanes.

Thus, these compounds may be used for preparing rigid foams, electric insulators, coatings, adhesives, flexible foams (notably in the field of furniture or of automobiles) or shoe soles.

More exactly, the compounds according to present invention are used for preparing rigid foams by reacting them with polyisocyanates in the presence of a catalyst and of a foaming agent (to which may also be added surfactants) coloring agents, antioxidants, preservatives, plasticizers, cross-linking agents, flame retardants, etc).

Preferably, such a rigid foam may be prepared by reacting the whole of the following constituents: 60 g of polyisocyanate, 40 g of polyol, 1.2 g of water (foaming agent), 0.1-0.4 g of catalyst and 1-4 g of surfactant.

More exactly, the polyols according to the present invention are used for preparing electric insulators by reacting them with polyisocyanates in the presence of an anti-foam agent and of a drying agent.

Preferably, such an electric insulator may be prepared by reacting together 60 g of polyol, 29 g of polyisocyanate, 0.6 g of anti-foam agent and 3 g of drying agent, and optionally 60 g of fillers (silica).

More exactly, the polyols according to the present invention are used for preparing coatings by reacting them with polyisocyanates. For example, coatings are prepared by using pure polyisocyanates and polyols, or by using polyols and polyisocyanates with solvents (it is also possible to add coloring agents, pigments, fillers, flow additives, antioxidants, bactericides, fungicides, corrosion inhibitors, catalysts or UV stabilizers).

For preparing adhesives according to the present invention, provision is also made for using the pure polyols of the invention with pure polyisocyanates.

As regards flexible foams, preferably, 60 g of polyol according to the invention, 100 g of isocyanate, 4.5 g of water (foaming agent), 0.12 g of catalyst 1, 0.38 g of catalyst 2 and 3 g of surfactant are used.

Finally, a specific formulation according to the invention for preparing shoe soles comprises 59 g of isocyanate, 94.5 g of polyol according to the invention, 4.1 g of ethylene glycol and 1.4 g of catalyst.

The present invention also relates to polymers such as those obtained by polymerization of a compound according to the present invention and of a (poly)isocyanate.

EXPERIMENTAL PART

Example 1

Preparation of Butanediol Esters

This example relates to the preparation of the compound (1) of the following formula:

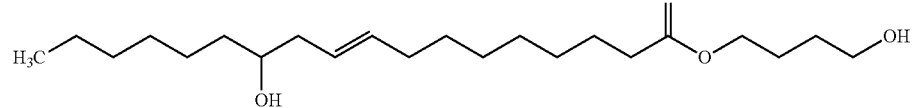

This is a compound of formula (I-1) wherein A represents a butylene radical.

The starting product is castor oil of formula:

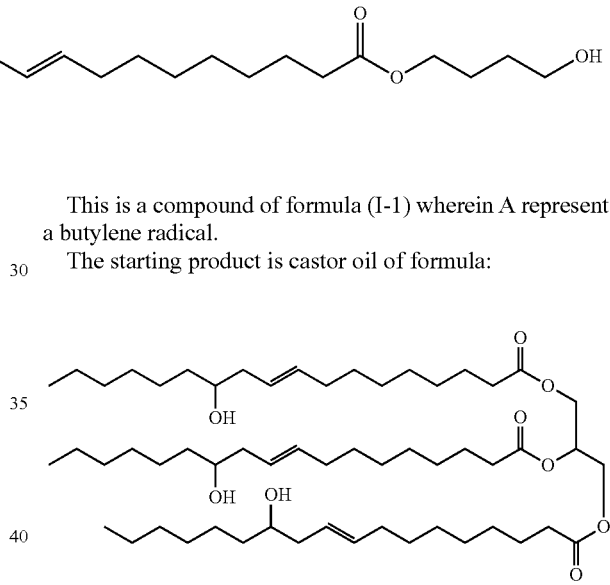

The castor oil used has the following mass composition of fatty acids:

| | |
|---|---|
| C16:0 | 1.1% |
| C18:0 | 1.3% |
| C18:1 | 3.4% |
| C18:2 | 4.5% |
| C18:3 | 0.1% |
| C18:OH | 88.5% |
| C20:0 | 0.1% |
| C20:1 | 0.5% |
| C22:0 | 0.5% |

In a reactor (2 liters), 167.8 g of castor oil (ITERG, M=928 g·mol$^{-1}$–acid index=0.65%–flash point=229° C.) are introduced with 1,556.4 g of 1,4-butanediol (Aldrich–M=90.12 g·mol$^{-1}$) and 2.4 g of MgO catalyst (Fluka). The butanediol is therefore in excess relatively to the castor oil with a butanediol/castor oil molar ratio of about 100.

The whole is mixed with stirring at 500 rpm and heated up to 150° C. A pale yellow coloration is then observed.

Next, the residual water was condensed around 100° C. and the whole was heated to 150-155° C. for 10 hours. Finally the reaction medium was left to rest overnight in the reactor.

In order to remove the butanediol, vacuum distillation under dinitrogen was carried out and the reaction medium was centrifuged to 500 rpm for 3 cycles of 15 minutes. The catalyst (MgO) was also filtered in vacuo on a Büchner.

In order to recover the final product, distillation under reduced pressure of said product was carried out at a temperature of 110-114° C. under a pressure of 3 to 5 mbars.

150 g of a translucent yellow oil were thereby obtained. This product has an acid index of 1.07% and a hydroxyl index of 273.1 mg KOH/g.

According to characterization by HPLC liquid chromatography which was carried out, the final product obtained has the following composition:

| | |
|---|---|
| Castor oil | 1.5% |
| Diester - compound of formula (I-2) | 4.7% |
| Monoester - compound (1) | 88.5% |
| Residual alcohol | 4.2% |
| Free fatty acid | 0.7% |
| Polymers | 0.0% |

Example 2

Preparation of Propanediol Esters

This example relates to the preparation of the compound (2) of the following formula:

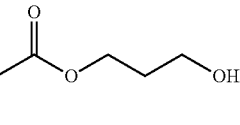

This is a compound of formula (I-1) wherein A represents a propylene radical.

The starting product is castor oil as described in Example 1.

In a reactor (4 liters), are introduced 250.5 g of castor oil (ITERG, M=928 g·mol$^{-1}$–acid index=0.65%–flash point=229° C.) with 2,052.8 g of 1,3-propanediol (Aldrich–M=76.09 g·mol$^{-1}$) and 3.9 g of MgO catalyst (Fluka). The propanediol is therefore in excess relatively to the castor oil with a propanediol/castor oil molar ratio of about 100.

The whole is mixed with stirring at 650 rpm and heated up to 150° C. A pale yellow coloration is then observed.

Next, the residual water was condensed around 100° C. and the whole was heated to 150° C. for 8 hours.

The whole was then left to decant in an ampoule in order to obtain a homogeneous phase. Next, a liquid-liquid extraction was carried out with hexane and two phases were observed: an upper yellow phase (hexane) and a cloudy lower phase (aqueous phase). The aqueous phase was then recovered and washed with hexane. The catalyst traces were also filtered on a Büchner. Finally, the solvents were evaporated with the Rotavapor and then washed with hot water (60° C.) and again evaporated and dried on the Rotavapor.

213 g of propanediol esters were thereby obtained. This product has an acid index of 2.68 KOH/mg and a hydroxyl index of 298.7 KOH/g.

According to the characterization by HPLC liquid chromatography which was carried out, the final obtained product has the following composition:

| | |
|---|---|
| Triglycerides | 1.3% |
| Diester - compound of the formula (I-2) | 2.8% |
| Monoester - compound (2) | 96.0% |
| Propanediol | 0.0% |
| Polymers | 0.0% |

A GPC analysis was then carried out with which it was possible to note the following mass composition:

| | |
|---|---|
| Triglycerides | 0.3% |
| Diester - compound of formula (I-2) | 1.7% |
| Monoester - compound (2) | 98.0% |
| Propanediol | 0.0% |
| Water and volatile substances | 0.27% |

Example 3

Preparation of Butanediol Diesters

This example relates to the preparation of the compound (3) of the following formula:

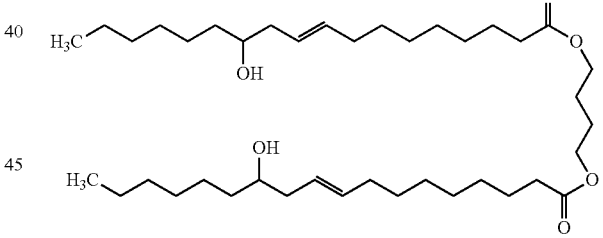

This is a compound of formula (I-2) wherein A represents a butylene radical.

The starting product is castor oil as described in Example 1.

The compound (3) was obtained according to a two-step method.

First Step: Synthesis of Castor Oil Ethyl Ester (4)

This step consists of preparing a castor oil ethyl ester of the following formula:

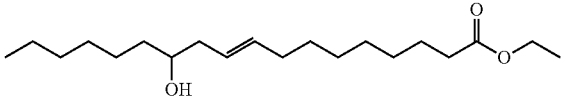 [SMILES: CCCCCCC(O)C/C=C/CCCCCCCC(=O)OCC]

In a jacketed reactor (1 liter), were introduced 402.4 g of castor oil (ITERG, M=928 g·mol$^{-1}$–water content=0.35% by weight) with 405.4 g of absolute ethanol (JT Baker–M=46.07 g·mol$^{-1}$). The whole is mixed with stirring at 650 rpm and heated to 65° C. 4.5214 g of MeONa (Aldrich-M=54.02 g·mol$^{-1}$) were then added into the reactor and a change in color of the product was then observed and the occurrence of instantaneous turbidity. The whole is then left to react for 30 minutes at 50° C.

The resulting reaction mixture was then transferred into a separating funnel in order to remove the glycerol and evaporate the ethanol. Neutralization was then carried out with a few drops of HCl followed by washing with water until neutrality. Finally, the residual water was distilled in the Rotavapor.

360.2 g of castor oil ethyl ester (4) were thereby obtained with a water content of 0.23% by weight.

According to the characterization by gas phase chromatography which was carried out, a composition was obtained comprising 93.8% by weight of ethyl ester (4).

Second Step: Synthesis of Castor Oil Butanediol Esters

The starting product is the compound (4) as obtained at the end of the first step.

In a reactor (500 mL), were introduced 300.5 g of compound (4) with 43.5 g (0.5 mol) of 1,4-butanediol (Aldrich)(a compound of formula (III) with A$_2$=butylene). The whole is heated to 65° C. 3.6005 g of MeONa (Aldrich) are then added into the reactor and a change in color of the product was then observed (opaque yellow), the whole is then left to react for 6 hours at 70-75° C. with stirring (650 rpm) at a pressure from 800 to 2 mbars.

Neutralization was then carried out with a few drops of HCl followed by washing with water in order to remove the traces of butanediol until neutrality. Finally the residual water was distilled in the Rotavapor.

260 g of castor oil butanediol ester of the aforementioned formula (3) were then obtained with a water content of 0.30% by weight. The product of formula (3) is in the form of a yellow liquid and has an acid index of 5.05%.

According to the characterization by gas phase chromatography which was carried out, a composition was obtained comprising 43.9% by weight of diesters (compound (3)) 30.4% by weight of monoesters and 25.7% by weight of compound (4).

Example 4

Preparation of Butanediol Esters

The obtained compound has the same formula as that of Example 1 but has a different composition.

In a reactor (2 liters) were introduced 505.3 g of castor oil with 698.9 g of 1,4-butanediol (Aldrich-M=90.12 g·mol$^{-1}$) and 7.5 g of MgO catalyst (Fluka). The butanediol is therefore in excess relatively to the castor oil.

The whole is mixed with stirring at 500 rpm and heated up to 150° C. A pale yellow coloration was then observed.

Next, the residual water was condensed around 100° C. and the whole was heated to 150-155° C. for 10 hours. Finally the reaction medium was left overnight at rest in the reactor.

The reaction mixture was centrifuged at 4,500 rpm for three times 15 minutes.

The catalyst (MgO) was also filtered in vacuo on a Büchner. In order to recover the final product, distillation of said product under reduced pressure was carried out at a temperature of 107° C. under a pressure of 1 mbar.

493 g of an orangey yellow oil were obtained. This product has an acid index of 0.95% and a hydroxyl index of 283.1 mg KOH/g.

According to the characterization by HPLC liquid chromatography which was carried out, the final product obtained has the following composition:

| | |
|---|---|
| Castor oil | 4.2% |
| Diester - compound of formula (I-2) | 12.3% |
| Monoester - compound of formula (I-1) | 79.4% |
| Residual alcohol | 3.7% |
| Free fatty acid | 0.4% |
| Polymers | 0.0% |

Example 5

Preparation of Butanediol Polyricinoleate

This example consists of preparing a castor oil estolide (butanediol polyricinoleate) of formula (I-4) with A=—(CH$_2$)$_4$— in several steps from castor oil.

First Step: Synthesis of Castor Oil Methyl Ester (5)

This step consists of preparing a castor oil methyl ester of the following formula:

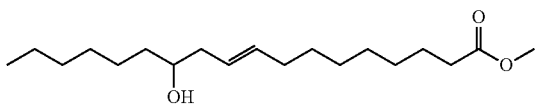 [SMILES: CCCCCCC(O)C/C=C/CCCCCCCC(=O)OC]

In a jacketed reactor (30 liters) were introduced 16,980 g of castor oil (ITERG, M=928 g·mol$^{-1}$–water content=0.35% by weight) with 4,393 g of methanol (Baker) and 454.12 g of MeONa (Aldrich). The whole is heated to 75° C. The temperature is maintained at 75° C. for 2 hours and then the reaction medium is cooled down to 40° C.

The resulting reaction mixture was then left to decant. Several washes with water and HCl were then carried out.

15,990 g of castor oil methyl ester (5) were thereby obtained.

Second Step: Synthesis of Castor Oil Estolides

The starting product is the compound (5) as obtained at the end of the first step.

In a reactor (1 L) were introduced 890.0 g of compound (5) with 13.9 g (1.56% w/w) of MeONa (Sigma-Aldrich). The whole is slowly heated in vacuo from 100° C. to 140° C., and then the reaction medium is maintained at 135° C. for one hour at atmospheric pressure.

841.5 g of castor oil estolide were thereby obtained in the form of a very dark viscous black/brown liquid

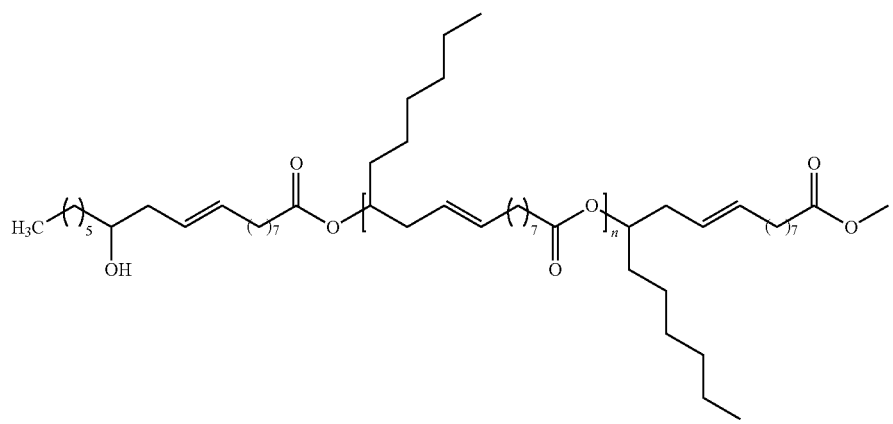

Third Step: Synthesis of Butanediol Castor Oil Estolides

This step consists of preparing a castor oil estolide of formula (I-4) with A=—(CH$_2$)$_4$—.

The starting product is the castor oil estolide obtained at the end of the previous step.

In a reactor (1 L), were introduced 458.0 g of estolide with 13.5 g (0.1 n) of butanediol (Sigma-Aldrich) and 2.2 g of MeONa (0.5% w/w). The whole is slowly heated in vacuo from 120° C. to 140° C.

Several decantation/washing steps were carried out (with HCl, NaCl and water).

320.5 g of butanediol castor oil estolide were thereby obtained in the form of a limpid orange/brown liquid.

Example 6

Preparation of Butanediol Polyricinoleate

This example consists of preparing a castor oil estolide of formula (I-4) with A=—(CH$_2$)$_4$—.

The starting product is the compound (5) as obtained at the end of the first step of Example 5.

In a reactor (250 mL), were introduced 150 g of compound (5) with 4.35 g (0.1 n) of 1,4-butanediol (Aldrich) and 1.5 g of MeONa (1% w/w). The whole is heated to 140° C. for 4 hours. A vacuum (500-700 mbars) is applied for about one hour and the pressure is reduced down to 150 mbars until the end of the reaction in order to remove the generated methanol. Once the reaction is complete, the reaction mixture was cooled down to room temperature and then dissolved in ethyl acetate (200 mL). The solution was washed with a 37% HCl solution and water until neutrality. The solvent was removed on a rotary evaporator in order to obtain a yellow liquid.

110.5 g of butanediol castor oil estolide (butanediol polyricinoleate) were thereby obtained.

According to the characterization by gas phase chromatography which was carried out, a composition was obtained comprising 56.40% by weight of estolide polymer.

This procedure was applied for the synthesis of castor oil estolides from butanediol by varying the amounts of butanediol, as indicated in the table below:

|  | Mass of compound (5) (g) | Mass of butanediol (g) | Mass of MeONa (g) | Mass of final product (g) |
| --- | --- | --- | --- | --- |
| Ex. 6.1 | 220 | 12.8 | 2.2 | 76.6 |
| Ex. 6.2 | 220 | 19.14 | 2.2 | 146.3 |
| Ex. 6.3 | 220 | 25.52 | 2.2 | 194.7 |
| Ex. 6.4 | 220 | 31.91 | 2.2 | 196.1 |

The final product is obtained as a mixture comprising compounds of the monomer type, of the dimer type and of the estolide type (butanediol polyricinoleate).

Example 7

Preparation of Polypropylene Glycol Polyricinoleate

This example consists of preparing a compound of formula (I-4) wherein A represents a polypropylene glycol unit.

The starting product is the compound (5) as obtained at the end of the first step of Example 5.

In a reactor (1 L), are introduced 500 g (1.61 mol) of compound (5) with 64.37% g (0.1 equiv.) of Voranol P400 (Bostik) and 5.48 g of Ti(OBu)$_4$ (1% n/n)(Sigma-Aldrich). The whole is heated in vacuo at 200° C. for 4 hours.

The reaction is conducted under 10 mbars in order to remove the generated methanol. Once the reaction is finished, the polyol is heated to room temperature in order to obtain a yellow liquid.

475.2 g of voranol castor oil estolide are thereby obtained.

This procedure was applied for the synthesis of castor oil estolides from voranol by varying the amounts of voranol, as indicated in the table below:

|  | Mass of compound (5) (g) | Mass of voranol (g) | Mass of Ti(OBu)$_4$ (g) | Mass of final product (g) |
| --- | --- | --- | --- | --- |
| Ex. 7.1 | 500 | 128.74 | 5.48 | 535.7 |
| Ex. 7.2 | 400 | 154.49 | 4.38 | 472.9 |
| Ex. 7.3 | 350 | 180.24 | 3.83 | 453.3 |
| Ex. 7.4 | 320 | 205.99 | 3.51 | 452 |

Example 8

Preparation of Polymers (Polyurethanes) from Polyols of the Invention

The polyols of the invention are used for preparing polymers for example by reaction with isocyanates. The applied procedure is described hereafter and may be applied to any polyol and to any isocyanate.

The polyol of the invention and the catalyst were added into a reactor of 1 liter and then the isocyanate (in particular IPDI or HDMI) were added into the reactor via a funnel. The whole is then stirred at 80 rpm under dinitrogen in order to homogenize the mixture. The occurrence of bubbles was then observed in the reaction mixture and the temperature of the mixture was maintained at 60° C. by heating.

Kinetic tracking of the reaction was carried out by IR analysis which gave the possibility of observing the disappearance of the N=C band at 2,269.94 cm$^{-1}$ and the appearance of the N—H band at 3,350 cm$^{-1}$.

More particularly, this procedure was applied by using as a polyol a castor oil butanediol monoester (the monoester compound of Example 4) and by varying the nature of the isocyanate (IPDI and HMDI), as well as the reaction time and the OH:NCO ratio.

The catalyst used is DBTDL (LCPO) dibutyl tin dilaurate) at 0.1% by weight.

The obtained results are summarized hereafter in Tables 1 and 2.

Table 1 corresponds to the synthesis of polyurethane by reaction with IPDI (Aldrich–M=222.29 g·mol$^{-1}$)(isophorone diisocyanate):

| | | | Solubility | | | Viscosity (cst) | | | |
| | | | (DCM, | | GPC | 80° C. | | 100° C. | |
| | | Reaction | THF, | | Analysis | Shearing (s$^{-1}$) | | | |
| No. | OH:NCO | time (h) | DMF) | IR Analysis | (Mw) | 1 | 10 | 1 | 10 |
|---|---|---|---|---|---|---|---|---|---|
| 1 | 1:0.3 | 6 | soluble | No isocyanate band | 1290 | — | 18 | — | 12.3 |
| 2 | 1:0.5 | 6 | soluble | No isocyanate band | 1890 | — | 41.5 | — | 19 |
| 3 | 1:0.66 | 4 | soluble | No isocyanate band | 2210 | 35 | 19.5 | — | 11.5 |
| 4 | 1:0.76 | 4 | soluble | No isocyanate band | 3710 | 275 | 205 | — | 75 |
| 5 | 1:0.87 | 4 | soluble | No isocyanate band | 5620 | 1015 | 1088 | 278 | 265 |
| 6 | 1:0.95 | 6 | soluble | No isocyanate band | 6640 | 2927 | 2839 | 531 | 563 |
| 7 | 1:1 | 6 | soluble | No isocyanate band | 9470 | — | — | — | — |
| 8 | 1:1.04 | 6 | soluble | No isocyanate band | 10750 | — | — | — | — |
| 9 | 1:1.15 | 6 | insoluble | — | — | — | — | — | — |

DCM: dichloromethane
THF: tetrahydrofurane
DMF: dimethylformamide

In order to obtain polyurethanes with satisfactory viscosity, it is therefore preferable to work at OH:NCO ratios of less than 1.

Table 2 corresponds to the synthesis of polyurethane by reaction with HMDI (hexamethylene diisocyanate):

| | | | Solubility | | | Viscosity (cst) | | | |
| | | | (DCM, | | GPC | 80° C. | | 100° C. | |
| | | Reaction | THF, | | Analysis | Shearing (s$^{-1}$) | | | |
| No. | OH:NCO | time (h) | DMF) | IR Analysis | (Mw) | 1 | 10 | 1 | 10 |
|---|---|---|---|---|---|---|---|---|---|
| 1 | 1:0.3 | 3 | soluble | No isocyanate band | 1410 | — | 11.8 | — | 6.6 |
| 2 | 1:0.5 | 3 | soluble | No isocyanate band | 2550 | — | 105 | — | 60 |
| 3 | 1:0.75 | 12 | soluble | No isocyanate band | 4060 | 620 | 563 | 163 | 148 |

The invention claimed is:

1. A compound of the following formula (I-4):

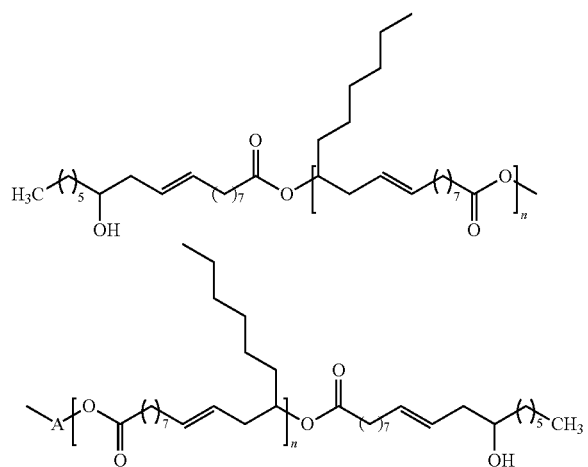

(I-4)

wherein:

n is comprised between 1 to 20; and

A represents a linear or branched divalent alkylene radical, comprising from 1 to 10 carbon atoms, and interrupted by one or more oxygen atoms.

2. The compound according to claim 1, wherein A represents an alkylene radical comprising 3 or 4 carbon atoms.

3. The compound according to claim 1, wherein A represents a (poly)propyleneglycol radical.

4. Polymers as obtained by polymerization of a compound as defined in claim 1 and of a (poly)isocyanate.

5. Polymers as obtained by polymerization of a compound as defined in claim 2 and of a (poly)isocyanate.

6. Polymers as obtained by polymerization of a compound as defined in claim 3 and of a (poly)isocyanate.

* * * * *